(12) United States Patent
Williams et al.

(10) Patent No.: US 11,311,884 B2
(45) Date of Patent: Apr. 26, 2022

(54) SAMPLE COLLECTION KIT INCLUDING CAP HAVING SELECTIVELY MOVABLE SLEEVE

(71) Applicant: Ancestry.com DNA, LLC, Lehi, UT (US)

(72) Inventors: Kevin Gregg Williams, Draper, UT (US); Jeremy Johnson, Riverton, UT (US); Bryce Twede, Provo, UT (US); Michael Andersen, Springville, UT (US); Michael S. Horito, Provo, UT (US); Collin Sorensen, Orem, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 393 days.

(21) Appl. No.: 16/198,480

(22) Filed: Nov. 21, 2018

(65) Prior Publication Data
US 2019/0151842 A1    May 23, 2019

Related U.S. Application Data

(60) Provisional application No. 62/625,187, filed on Feb. 1, 2018, provisional application No. 62/590,165, filed on Nov. 22, 2017.

(51) Int. Cl.
*B01L 3/00* (2006.01)

(52) U.S. Cl.
CPC .......... *B01L 3/508* (2013.01); *B01L 3/50825* (2013.01); *B01L 3/523* (2013.01);
(Continued)

(58) Field of Classification Search
CPC ...... B01L 3/508; B01L 3/50825; B01L 3/523; B01L 2200/0689; B01L 2200/087;
(Continued)

(56) References Cited

U.S. PATENT DOCUMENTS

| 718,127 A | 1/1903 | Holmgren |
| D169,994 S | 7/1953 | Soffer et al. |

(Continued)

FOREIGN PATENT DOCUMENTS

| EP | 3235441 A1 | 10/2017 |
| JP | 2010-213660 A | 9/2010 |

(Continued)

OTHER PUBLICATIONS

Meulenbelt, I. et al. "High-Yield Noninvasive Human Genomic DNA Isolation Method for Genetic Studies in Geographically Dispersed Families and Populations," American Journal of Human Genetics, 1995, vol. 57, No. 1252-1254, 3 pages.

(Continued)

*Primary Examiner* — Jennifer Wecker
*Assistant Examiner* — Oyeleye Alexander Alabi
(74) *Attorney, Agent, or Firm* — Fenwick & West LLP

(57) ABSTRACT

A biological sample collection system can include a sample collection vessel having a sample collection chamber with an opening configured to receive a biological sample into the sample collection chamber. The biological sample collection system can additionally include a selectively movable sleeve valve configured to associate with the opening of the sample collection chamber. The biological sample collection system can additionally include a sealing cap that is configured to associate with the selectively movable sleeve valve and with the sample collection vessel. The sealing cap can include a reagent chamber having reagent(s) stored therein, and when the sealing cap is associated with the sample collection vessel, the selectively movable sleeve valve opens, dispensing the reagent(s) into the sample collection chamber.

27 Claims, 6 Drawing Sheets

(52) U.S. Cl.
CPC . *B01L 2200/0689* (2013.01); *B01L 2200/087* (2013.01); *B01L 2200/16* (2013.01); *B01L 2300/042* (2013.01); *B01L 2300/047* (2013.01); *B01L 2300/049* (2013.01); *B01L 2300/0832* (2013.01)

(58) Field of Classification Search
CPC .......... B01L 2200/16; B01L 2300/042; B01L 2300/047; B01L 2300/049; B01L 2300/0832
See application file for complete search history.

(56) References Cited

U.S. PATENT DOCUMENTS

| | | | |
|---|---|---|---|
| D175,257 S | 8/1955 | Hopkins | |
| 2,793,776 A | 5/1957 | Ipari | |
| D196,112 S | 8/1963 | Esser | |
| 3,831,742 A | 8/1974 | Gardella et al. | |
| 4,131,016 A | 12/1978 | Layton | |
| 4,184,483 A | 1/1980 | Greenspan | |
| 4,217,798 A | 8/1980 | McCarthy et al. | |
| 4,301,812 A | 11/1981 | Layton et al. | |
| 4,312,950 A | 1/1982 | Snyder et al. | |
| D277,736 S | 2/1985 | Long | |
| D286,546 S | 11/1986 | Funahashi | |
| 4,935,342 A | 6/1990 | Seligson et al. | |
| 4,982,553 A | 1/1991 | Itoh | |
| D330,011 S | 10/1992 | Miller | |
| 5,283,038 A | 2/1994 | Seymour | |
| 5,393,496 A | 2/1995 | Seymour | |
| 5,396,986 A | 3/1995 | Fountain et al. | |
| D362,623 S | 9/1995 | Ma | |
| 5,714,341 A | 2/1998 | Thieme et al. | |
| D392,187 S | 3/1998 | King | |
| 5,736,322 A | 4/1998 | Goldstein | |
| 5,736,355 A | 4/1998 | Dyke et al. | |
| 5,830,154 A | 11/1998 | Goldstein et al. | |
| 5,830,410 A | 11/1998 | Thieme et al. | |
| D412,107 S | 7/1999 | Bosshardt | |
| 5,927,549 A | 7/1999 | Wood | |
| 5,933,498 A | 8/1999 | Schneck et al. | |
| 6,003,728 A | 12/1999 | Elliott | |
| 6,048,091 A | 4/2000 | McIntyre et al. | |
| 6,152,296 A | 11/2000 | Shih | |
| D437,786 S | 2/2001 | van Swieten et al. | |
| 6,228,323 B1 | 5/2001 | Asgharian et al. | |
| 6,428,962 B1 | 8/2002 | Naegele | |
| 6,458,546 B1 | 10/2002 | Baker | |
| D470,240 S | 2/2003 | Niedbala et al. | |
| D471,234 S | 3/2003 | Okutani | |
| 6,543,612 B2 | 4/2003 | Lee et al. | |
| 6,548,256 B2 | 4/2003 | Lienau et al. | |
| D474,280 S | 5/2003 | Niedbala et al. | |
| 6,627,152 B1 | 9/2003 | Wong | |
| 6,786,330 B2 | 9/2004 | Mollstam et al. | |
| D507,351 S | 7/2005 | Birnboim | |
| 6,939,672 B2 | 9/2005 | Lentrichia et al. | |
| 6,992,182 B1 | 1/2006 | Müller et al. | |
| D515,435 S | 2/2006 | Muehlhausen | |
| 7,055,685 B1 | 6/2006 | Patterson et al. | |
| D537,416 S | 2/2007 | Fortin et al. | |
| 7,178,683 B2 | 2/2007 | Birkmayer et al. | |
| 7,214,484 B2 | 5/2007 | Weber et al. | |
| 7,297,485 B2 | 11/2007 | Bornar et al. | |
| 7,303,876 B2 | 12/2007 | Greenfield et al. | |
| D573,465 S | 7/2008 | Kogure et al. | |
| D574,507 S | 8/2008 | Muir et al. | |
| D584,357 S | 1/2009 | Oka | |
| 7,482,116 B2 | 1/2009 | Birnboim | |
| D586,856 S | 2/2009 | Yagyu | |
| 7,537,132 B2 | 5/2009 | Marple et al. | |
| 7,544,468 B2 | 6/2009 | Goldstein et al. | |
| 7,589,184 B2 | 9/2009 | Hogan et al. | |
| 7,645,424 B2 | 1/2010 | O'Donovan | |
| D612,730 S | 3/2010 | Rushe | |
| 7,748,550 B2 | 7/2010 | Cho | |
| 7,854,104 B2 | 12/2010 | Cronin et al. | |
| 7,858,396 B2 | 12/2010 | Corstjens et al. | |
| D631,350 S | 1/2011 | Beach et al. | |
| D631,553 S | 1/2011 | Niedbala et al. | |
| D640,794 S | 6/2011 | Sunstrum et al. | |
| D640,795 S | 6/2011 | Jackson et al. | |
| 7,998,757 B2 | 8/2011 | Darrigrand et al. | |
| 8,038,668 B2 | 10/2011 | Scott et al. | |
| 8,062,908 B2 | 11/2011 | Mink et al. | |
| 8,158,357 B2 | 4/2012 | Birnboim et al. | |
| 8,221,381 B2 | 7/2012 | Muir et al. | |
| D673,265 S | 12/2012 | Nonnemacher et al. | |
| 8,425,864 B2 | 4/2013 | Haywood et al. | |
| 8,431,384 B2 | 4/2013 | Hogan et al. | |
| 8,470,536 B2 | 6/2013 | Birnboim et al. | |
| D693,682 S | 11/2013 | Bahri et al. | |
| 8,673,239 B2 | 3/2014 | Niedbala et al. | |
| 8,728,414 B2 | 5/2014 | Beach et al. | |
| D718,127 S | 11/2014 | Moriyama | |
| 9,040,675 B2 | 5/2015 | Bales et al. | |
| 9,072,499 B2 | 7/2015 | Birnboim et al. | |
| 9,079,181 B2 | 7/2015 | Curry et al. | |
| D743,044 S | 11/2015 | Jackson et al. | |
| D743,571 S | 11/2015 | Jackson et al. | |
| 9,207,164 B2 | 12/2015 | Muir et al. | |
| D757,546 S | 5/2016 | Seifer | |
| 9,410,147 B2 | 8/2016 | Gundling | |
| 9,416,356 B2 | 8/2016 | Gundling | |
| 9,523,115 B2 | 12/2016 | Birnboim | |
| D775,953 S | 1/2017 | Ruthe-Steinsiek | |
| D777,111 S | 1/2017 | Zantout et al. | |
| 9,732,376 B2 | 8/2017 | Oyler et al. | |
| 9,757,179 B2 | 9/2017 | Formica | |
| D811,882 S | 3/2018 | Gundersen | |
| 10,000,795 B2 | 6/2018 | Birnboim et al. | |
| D843,834 S | 3/2019 | Gundersen | |
| D850,647 S | 6/2019 | Jackson et al. | |
| 10,435,735 B2 | 10/2019 | Birnboim et al. | |
| 2003/0089627 A1 | 5/2003 | Chelles et al. | |
| 2004/0132091 A1 | 7/2004 | Ramsey et al. | |
| 2006/0201948 A1 | 9/2006 | Ellson et al. | |
| 2007/0170142 A1 | 7/2007 | Cho | |
| 2009/0024060 A1 | 1/2009 | Darrigrand et al. | |
| 2009/0133366 A1* | 5/2009 | Cronin | B65D 47/243 53/420 |
| 2009/0216213 A1 | 8/2009 | Muir et al. | |
| 2010/0099149 A1 | 4/2010 | Birnboim et al. | |
| 2010/0258457 A1 | 10/2010 | Seelhofer | |
| 2011/0020195 A1 | 1/2011 | Luotola | |
| 2011/0207621 A1 | 8/2011 | Montagu et al. | |
| 2011/0212002 A1 | 9/2011 | Curry et al. | |
| 2012/0024861 A1 | 2/2012 | Otsuka et al. | |
| 2012/0024862 A1 | 2/2012 | Otsuka et al. | |
| 2012/0046574 A1 | 2/2012 | Skakoon | |
| 2012/0061392 A1 | 3/2012 | Beach et al. | |
| 2013/0092690 A1 | 4/2013 | Skakoon | |
| 2013/0164738 A1 | 6/2013 | Becker | |
| 2014/0120531 A1* | 5/2014 | Biadillah | B01L 3/502 435/6.1 |
| 2014/0316302 A1 | 10/2014 | Nonnemacher et al. | |
| 2015/0056716 A1 | 2/2015 | Oyler et al. | |
| 2016/0262679 A1 | 9/2016 | Ivosevic et al. | |
| 2017/0001191 A1 | 1/2017 | Biadillah et al. | |
| 2017/0072393 A1 | 3/2017 | Jackson et al. | |
| 2017/0130219 A1 | 5/2017 | Birnboim et al. | |
| 2017/0166955 A1 | 6/2017 | Birnboim et al. | |
| 2017/0226469 A1 | 8/2017 | Birnboim et al. | |
| 2019/0151842 A1 | 5/2019 | Williams et al. | |
| 2019/0210778 A1 | 7/2019 | Muir et al. | |
| 2019/0358628 A1 | 11/2019 | Curry et al. | |

FOREIGN PATENT DOCUMENTS

| | | |
|---|---|---|
| WO | WO-98/03265 | 1/1998 |
| WO | WO-2012/177656 A2 | 12/2012 |

(56) References Cited

FOREIGN PATENT DOCUMENTS

| WO | WO 2015/017701 A1 | 2/2015 |
|----|-------------------|--------|
| WO | WO 2015/112496 A2 | 7/2015 |
| WO | WO-2016/178132 A1 | 11/2016 |

OTHER PUBLICATIONS

PCT International Search Report and Written Opinion, PCT Application No. PCT/US2018/062312, dated Mar. 19, 2019, fifteen pages.
PCT International Search Report and Written Opinion, PCT International Patent Application No. PCT/US2020/023711, dated Jul. 16, 2020, 12 pages.
United States Office Action, U.S. Appl. No. 29/686,155, filed Jul. 23, 2020, 7 pages.
European Patent Office, Extended European Search Report and Opinion, EP Patent Application No. 18881701.9, dated Jul. 1, 2021, eight pages.

* cited by examiner

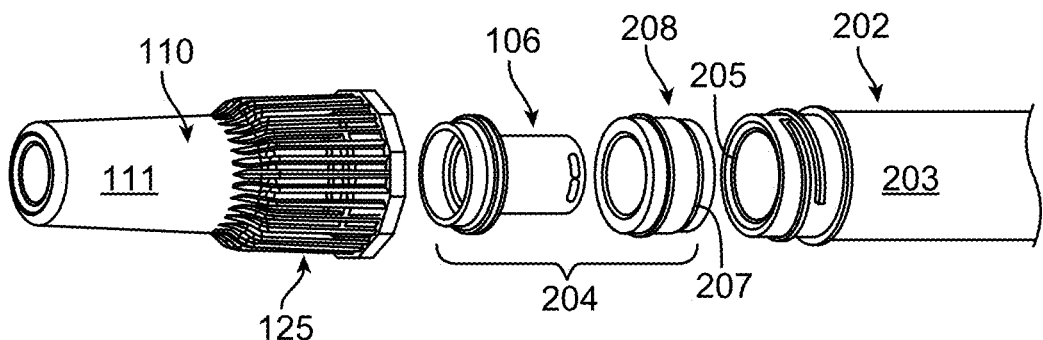
FIG. 7
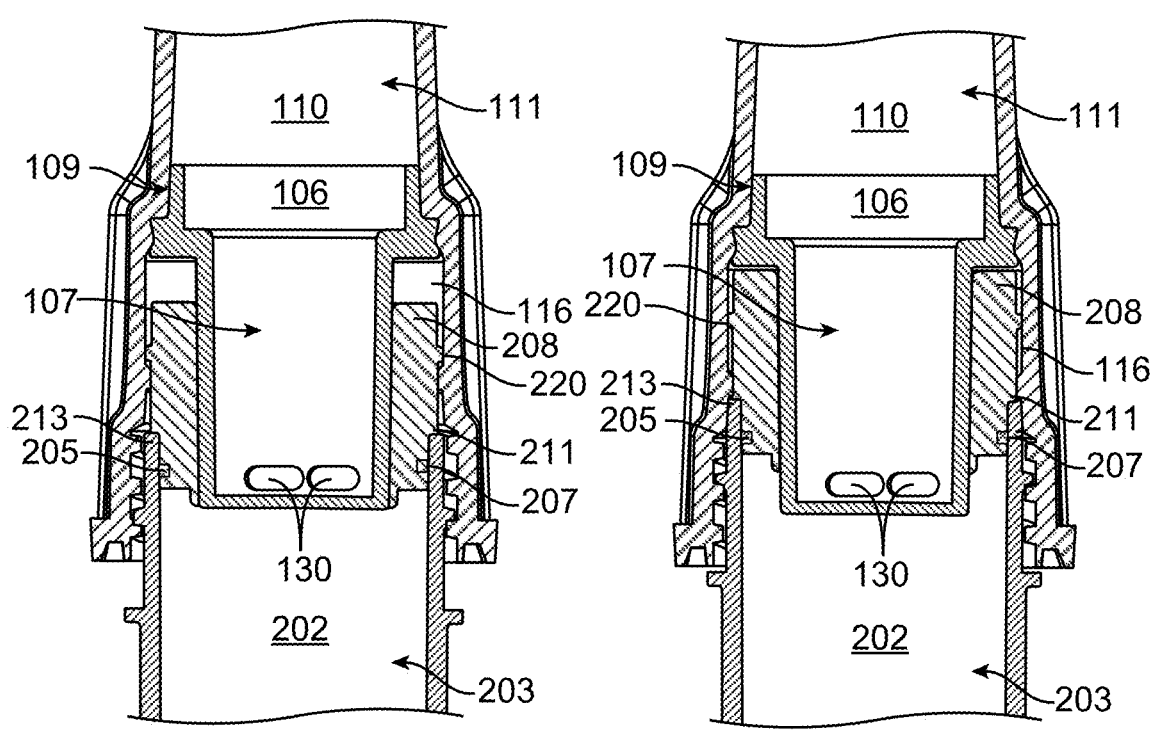
FIG. 8
FIG. 9

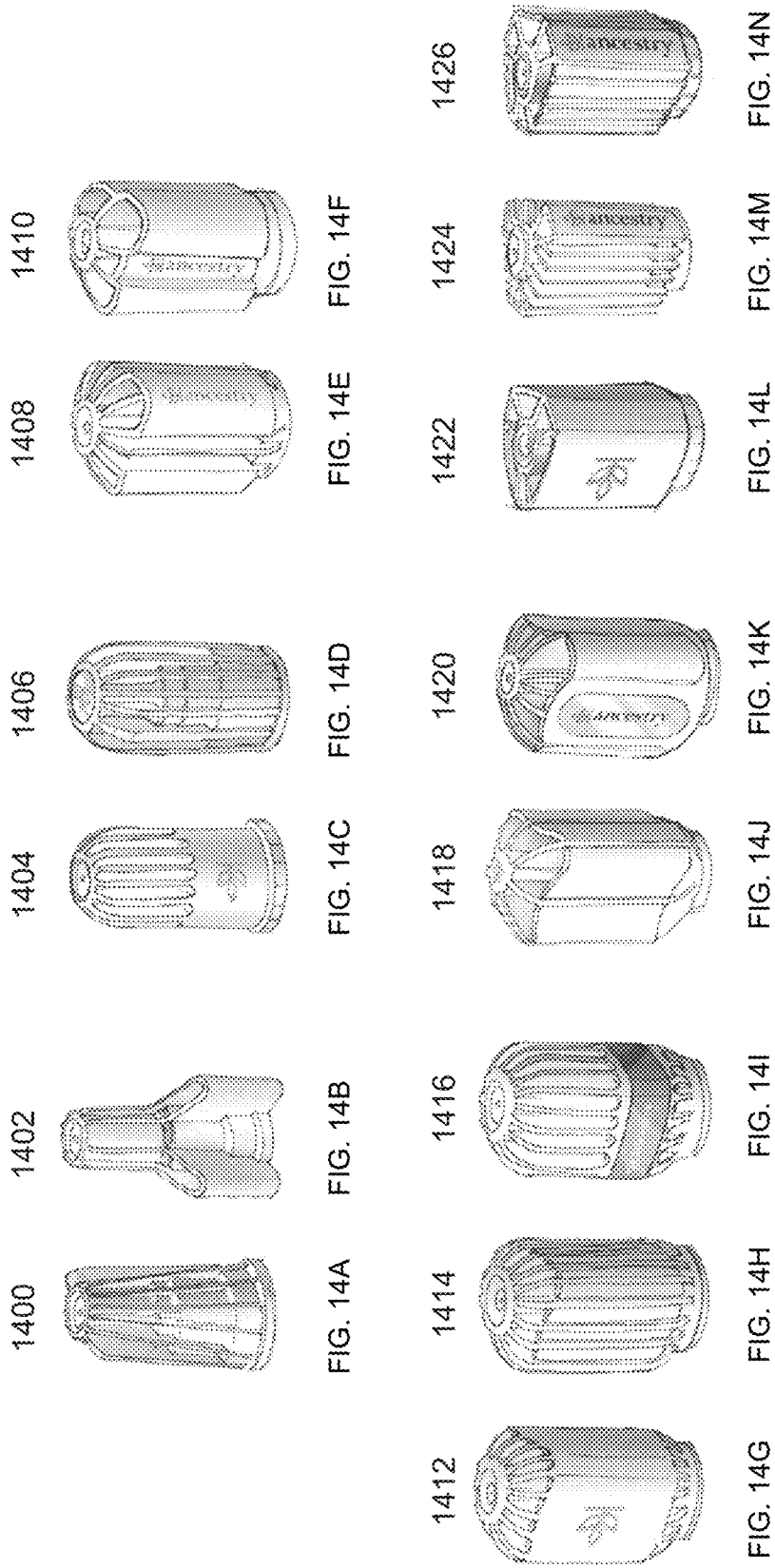

SAMPLE COLLECTION KIT INCLUDING CAP HAVING SELECTIVELY MOVABLE SLEEVE

CROSS-REFERENCE TO RELATED APPLICATIONS

This application claims priority to U.S. Provisional Patent Application No. 62/590,165, filed Nov. 22, 2017, and to U.S. Provisional Patent Application No. 62/625,187, filed Feb. 1, 2018, both of which are incorporated herein by reference in their entirety.

BACKGROUND

This disclosure generally relates to vials and vessels for collecting and storing biological samples. More specifically, the present disclosure relates to systems and kits for the collection and preservation of biological samples for future testing in a laboratory or other biological sample analysis facility.

Field collection of biological samples can provide scientists, physicians, geneticist, epidemiologists, or similar personnel with invaluable information. For example, access to a fresh sample of a patient's blood, purulent discharge, or sputum can help a physician or epidemiologist to isolate or identify a causative agent of infection. Similarly, a saliva sample can permit a scientist or geneticist access to the requisite nucleic acid for genetic sequencing, phylotyping, or other genetic-based studies. In the foregoing examples, in addition to many other situations, it is desirable to work with a fresh biological sample to ensure procurement of accurate results. However, isolation of the probative composition (e.g., nucleic acid, proteins, chemicals, etc.) often requires use of specialized equipment and often benefits from controlled laboratory conditions.

It can be inconvenient and sometimes improbable to require patients/individuals to travel to a biological sample collection center having the appropriate equipment and desirable controlled environment for sample preparation. Similarly, it may be difficult for personnel to directly access the patient/individual, particularly if the sample size is large and/or geographically diverse (e.g., as can be found in large genetic studies of thousands of individuals across an entire country, ethnic population, or geographic region). Further complicating this issue, it is often beneficial to immediately process any procured biological sample, and field personnel may be limited by lack of access to appropriate specialized equipment or to a controlled environment for high-fidelity sample processing.

Some biological sample collection devices and kits have addressed some of the foregoing issues. For example, some commercial kits provide a user with a vial for receiving a biological sample and a preservation reagent that can be added to the collected biological sample, acting to preserve elements within the biological sample (to a certain extent and for a period of time). However, implementations of self-collection systems often rely on inexperienced or untrained individuals to deposit the biological sample into the receiving vessel. This presents a number of problems, including, for example, technical training and precise measurements often required to properly preserve the biological sample for later processing. In the absence of such, it is important to provide a biological sample collection system that can be easily implemented by a novice user and which can preserve the received biological sample for later processing.

Accordingly, there are a number of disadvantages with biological sample collection and preservations systems that can be addressed.

SUMMARY

Implementations of the present disclosure solve one or more of the foregoing or other problems in the art with kits, apparatuses, and methods for collecting and preserving a biological sample. In particular, one or more implementations can include a kit for collecting and preserving a biological sample. The kit can include a sample collection vessel having a sample collection chamber with an opening configured to receive a biological sample from a user. The sample collection vessel can also include a connection member (e.g., one or more threads) disposed on an exterior portion of the sample collection vessel and adjacent to the opening. The kit can also include a sealing cap having a reagent chamber that stores a measure of reagent(s) and a complementary connection member that is configured to engage the connection member of the sample collection vessel. The kit can also include a selectively movable sleeve valve configured to associate with the sealing cap and with the opening of the sample collection chamber.

The present disclosure also includes biological sample collection systems. In some embodiments, a biological sample collection system includes a sample collection vessel having a sample collection chamber with an opening configured to receive a biological sample into the sample collection chamber. The biological sample collection system can additionally include a selectively movable sleeve valve configured to associate with the opening of the sample collection chamber. The biological sample collection system can additionally include a sealing cap that is configured to associate with the selectively movable sleeve valve and with the sample collection vessel. The sealing cap can include a reagent chamber having reagent(s) stored therein, and when the sealing cap is associated with the sample collection vessel, the selectively movable sleeve valve opens, dispensing the reagent(s) into the sample collection chamber.

The present disclosure also includes methods for collecting and preserving a biological sample. An exemplary method includes receiving a biological sample at a sample collection vessel and associating a sealing cap with the sample collection vessel to cause a selectively movable sleeve valve associated with the sealing cap to open and thereby release reagent(s) held within the sealing cap into the sample collection chamber. In some embodiments, associating the sealing cap with the sample collection vessel includes threadedly engaging a connection member disposed on an exterior surface of the sample collection vessel with a complementary connection member disposed on an interior surface of the sealing cap. The rotational force of threadedly engaging the sealing cap and the sample collection vessel moves an inner vessel of the selectively movable sleeve valve through an aperture defined by an outer sleeve of the selectively movable sleeve valve—and to which it is in fluid-tight association—to expose a fluid vent defined by the distal portion of the inner vessel. In other words, the selectively movable sleeve valve is open. In some embodiments, at least partially disassociating the sealing cap from the sample collection vessel (e.g., applying a directionally opposite rotational force used to threadedly associate the sealing cap and the sample collection vessel) causes the inner vessel to retreat back into the aperture defined by the outer sleeve, obstructing the fluid vent, or in other words, at least partially disassociating the sealing cap from the sample collection vessel closes the selectively movable sleeve valve.

Accordingly, systems, methods, and kits for collecting a biological sample are disclosed herein. This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIG. 7 illustrates an exploded perspective view of a three-dimensional model of a sample collection system.

FIG. 8 illustrates a cross-sectional, assembled view of the sample collection system of FIG. 7 with the selectively movable sleeve valve depicted in a sealed/resealed configuration.

FIG. 9 illustrates a cross-sectional, assembled view of the sample collection system of FIG. 7 with the selectively movable sleeve valve depicted in an unsealed configuration.

FIGS. 14A-14N illustrate perspective views of various embodiments of a sealing cap.

DETAILED DESCRIPTION

Figure 1:
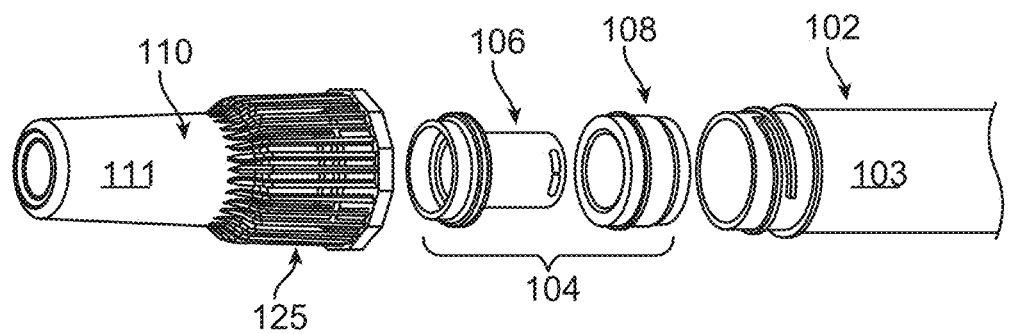
FIG. 1 illustrates an exploded view of a three-dimensional model of a sample collection system that includes a cap configured to receive a selectively movable sleeve valve.

Embodiments of the present disclosure address one or more problems in the art of systems, kits, and/or methods for collecting and preserving a biological sample. A biological sample can be collected and its contents evaluated for various reasons, including, for example, identifying or characterizing a causative agent of disease (e.g., for treatment of the affected individual, for epidemiological reasons, etc.) or for genetic analysis of a subject's nucleic acid (e.g., genetic phylotyping, gene expression studies, genome sequencing, etc.). In most instances, including within the foregoing examples, it is desirous that the fidelity of the biological sample is maintained so that it retains its probative value. However, collecting and preparing biological samples for analysis has traditionally been an endeavor for the skilled technician or specialized professional. This is problematic for obvious reasons, including the time and cost associated with individually collecting and transporting biological samples, particularly when the subjects reside in disparate rural locations and require service from personnel with the proper skill set to properly collect and preserve the biological sample.

Embodiments of the present disclosure provide sample collection and preservation systems and kits, and methods for using the same, which address one or more of the foregoing problems. For example, utilizing systems, kits, and methods for collecting and preserving biological samples, as disclosed herein, remove the need of specialized personnel when collecting and initially preserving a biological sample. Furthermore, sample collection and preservation are simplified, which decreases the likelihood that even an unskilled user will err when collecting and preserving a biological sample. As an illustrative example of the foregoing, biological sample collection kits disclosed herein include at least a two-piece sample collection and preservation system. A first portion includes a sample collection vial or vessel, which can be detachably associated with a funnel. When used, the funnel acts to guide the receipt of a biological sample from a user into the sample collection chamber of the collection vial or vessel. The funnel can also make it easier for a user to engage the collection vial and deposit a biological sample into the sample collection chamber. After depositing the requisite amount of biological sample, a user can remove the funnel (if used) and associate the second portion of the two-piece sample preservation system—e.g., a sealing cap associated with a reagent chamber—with the collection vial. The reagent chamber has been pre-filled with a predetermined amount of sample preservation reagent(s), and as the sealing cap is drawn down to seal the received biological sample within the sample collection chamber, the reagent(s) are released from the reagent chamber and into the sample collection chamber, mixing with and preserving the received biological sample.

As described in more detail below, the reagent chamber can be opened to release reagents into the sample collection chamber in a plurality of ways. In some embodiments, the reagent chamber is associated with a selectively movable sleeve valve, and when the sealing cap and reagent chamber are associated with the collection vial, the selectively movable sleeve valve opens (e.g., by undergoing a physical rearrangement), permitting previously obstructed fluid vent(s) to communicate fluid between the reagent compartment and the sample collection chamber. Reagent(s) in the reagent compartment can be released into the sample collection chamber through the fluid vent(s). In some embodiments, the opening of the selectively movable sleeve valve is reversible. For example, disassociating the sealing cap from the sample collection vial or vessel can cause the selectively movable sleeve valve to close.

As can be appreciated from the foregoing, in addition to alternative and/or additional embodiments provided herein, the systems, kits, and methods of the present disclosure can be used by skilled or unskilled individuals with reduced likelihood of error associated with collecting and at least initially preserving a biological sample. Accordingly, implementations of the present disclosure can reduce the cost associated with procuring biological samples for diagnostic, scientific, or other purposes and can increase the geographic reach of potential sample collection areas without the need of establishing the necessary infrastructure (e.g., controlled environments conducive to sample collection and preservation, skilled personnel to physically collect, transport, and/or preserve the biological samples, etc.).

As used herein, the term "biological sample" can include any cell, tissue, or secretory fluid (whether host or pathogen related) that can be used for diagnostic, prognostic, genetic, or other scientific analysis. This can include, for example, a human cell sample such as skin. It can also include a non-human cell sample that includes any of a bacterium, virus, protozoa, fungus, parasite, and/or other prokaryotic or eukaryotic symbiont, pathogen, or environmental organism. The term "biological sample" is also understood to include fluid samples such as blood, urine, saliva, and cerebrospinal fluid and extends to other biological samples including, for example, mucus from the nasopharyngeal region and the lower respiratory tract (i.e., sputum).

As used herein, the "probative component" of the biological sample refers generally to any protein, nucleic acid, surface moiety, or other compound that can be isolated from the biological sample. Preferably, the probative component is or includes nucleic acid, more preferably DNA. In a preferred embodiment, the biological sample is or includes saliva, which presumptively contains a preferable probative component in the form of the user's genetic material (e.g., DNA and RNA).

A Multi-Part Self-Contained Sample Collection System/Kit

In one embodiment, a biological sample is collected, preserved, and stored in a collection vessel as part of a multi-piece, self-contained sample collection system or kit. A first piece of the system or kit includes a collection vessel, a second piece includes a sample collection funnel, which may be packaged separately from or removably connected to the collection vessel, and a third piece includes a sealing cap having a selectively movable sleeve valve comprised of an inner vessel and an outer sleeve and a reagent chamber disposed within or integrated with the sealing cap. The sealing cap is configured to associate with the collection vessel, to dispense sample preservation reagents into the collection vessel through the selectively movable sleeve valve, and to seal the contents therein.

For example, FIG. 1 illustrates an exploded view of a three-dimensional model depicting a biological sample collection system or kit 100. The system 100 includes a collection vessel 102 and optionally, a funnel (not shown), which can be associated with a top portion of the collection vessel 102 and in fluid communication with a sample collection chamber 103 of the collection vessel 102. The biological sample collection system 100 can also include a selectively movable sleeve valve 104 comprised of an inner vessel 106 and an outer sleeve 108 associated with a sealing cap 110 that has a reagent chamber 111 disposed within or integrated with the sealing cap 110. The sealing cap 110—together with the selectively movable sleeve valve 104—can be sized and shaped to associate with a top portion of the collection vial 102, fitting over and sealing an opening of the sample collection chamber 103.

In some embodiments, the reagent(s) within the reagent chamber 111 include a preservation or buffering solution that protect the integrity of the probative component of the biological sample prior to purification or testing. Preservation reagents are typically chemical solutions and may contain one or more salts (e.g., NaCl, KCl, $Na_2HPO_4$, $KH_2PO_4$, or similar, and which may, in some implementations, be combined as a phosphate buffered saline solution, as known in the art), lysing agents (e.g., detergents such as Triton X-100 or similar), chelating agents (e.g., ethylenediaminetetraacetic acid (EDTA), ethylene glycol-bis(β-aminoethyl ether)-N,N,N',N'-tetraacetic acid (EGTA), or similar), distilled water, or other reagents known in the art. In one or more embodiments, the reagent or buffering solution stabilizes at least one probative component within the sample (e.g., nucleic acids, such as DNA and RNA, protein, etc., and combinations thereof) during transfer, transportation, and/or storage at a laboratory, clinic, or other destination. In some embodiments, the sample can be stored, at or below room temperature after the preservation solution is added, for weeks or months without significant loss of the probative component. That is, the sample can still be utilized for diagnostic, genetic, epidemiologic, or other purposes for which it was collected after storage for weeks or months in the preservation solution.

Figures 2, 3:
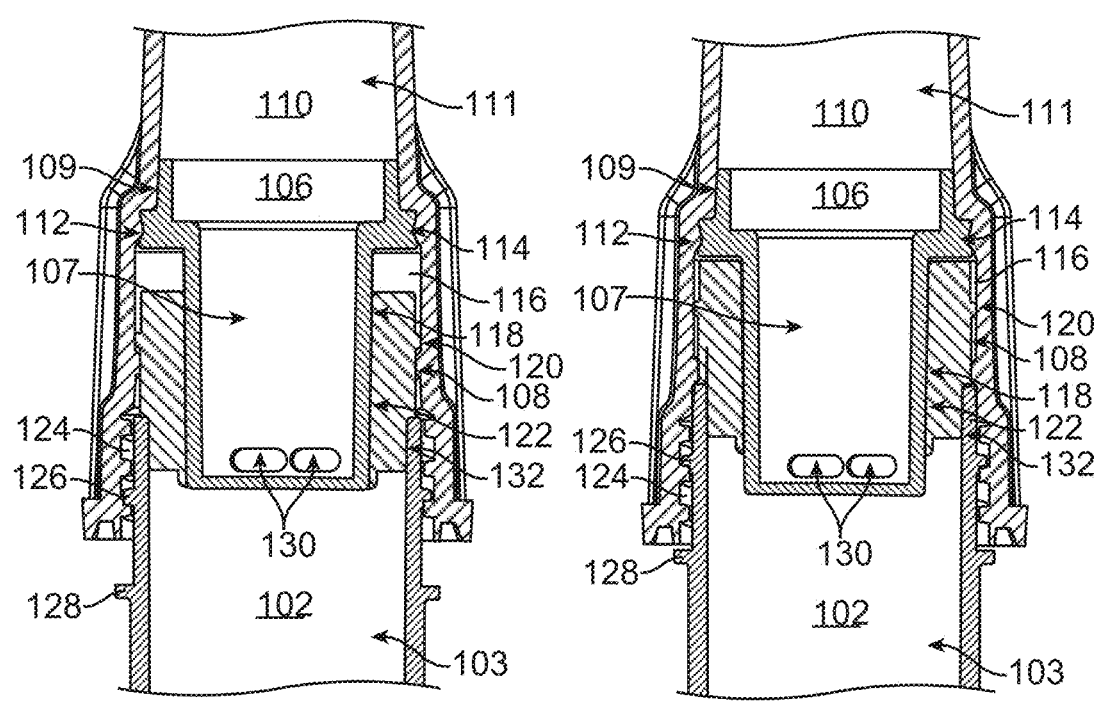
FIG. 2 illustrates a cross-sectional view of an assembled sample collection system with the selectively movable sleeve valve depicted in a closed position.
FIG. 3 illustrates a cross-sectional view of the assembled sample collection system of FIG. 2 with the selectively movable sleeve valve is depicted in an open position.

With continued reference to FIG. 1, the sealing cap 110 and a saliva funnel (not shown) can each independently attach to the sample collection vessel 102 using a connection mechanism. The connection mechanism can include, for example, threads, snap or press fit connections, tongue and groove members, bayonet connection, or other interlocking or mechanically coupling mechanisms. For example, a funnel can be first attached to the sample collection vessel 102 via complementary connection mechanisms (e.g., complementary threads; not shown). After facilitating receipt of a biological sample from a user, the funnel can be removed by reversing the complementary connection mechanism (e.g., unscrewing the funnel; not shown), and a sealing cap 110 can be secured to the collection vessel 102 using a same or similar complementary connection mechanism, as shown in FIG. 2. That is, the sealing cap 110 can include connection members 126 (e.g., threads) located on an inner circumferential wall of the sealing cap 110 that are complementary to and work in conjunction with the connection members 124 (e.g., complementary threads) disposed on an exterior surface of the sample collection vessel 102.

In some embodiments, the connection mechanism between the funnel and collection vial is different than the connection mechanism between the solution cap and the collection vial. For example, the funnel may be press fit or snap fit onto the collection vial, whereas the solution cap is rotationally secured through engagement of complementary threads located on an exterior portion of the collection vial and an interior portion of the solution cap or vice versa. Regardless of the attachment mechanism used, a sample preservation fluid can be introduced into the sample collection chamber 103 of the sample collection vessel 102 and mixed with the deposited biological sample as a result of the sealing cap 110 being attached to the sample collection vessel 102. As provided earlier, this can be due to the selectively movable sleeve valve 104 opening and allowing reagent(s) to be released through fluid vents 130 defined by the selectively movable sleeve valve 104 and into the sample collection chamber 103.

In an embodiment, the sealing cap 110 receives a measure of reagents into the reagent chamber 111, and as shown by the cross-sectional views of the assembled biological sample collection system 100A in FIG. 2, a selectively movable sleeve valve 104 (in a closed configuration) is associated with the sealing cap 110, sealing the reagents within the sealing cap 110. The inner vessel 106 is snap-fittingly received into the sealing cap 110 creating a fluid tight connection. As illustrated, the inner vessel includes a retaining ring 114 into which a protrusion 112 of the interior sidewall of the sealing cap 110 inserts to stabilize the inner vessel 106. In some embodiments, the interaction between the protrusion 112 and the retaining ring 114 creates the fluid tight connection between the sealing cap 110 and the inner vessel 106. Additionally, or alternatively, an upper collar 109 of the inner vessel extends into the reagent chamber 111 and associates there via an interference fit, creating a fluid tight connection between the interior sidewall of the reagent chamber 111 and the exterior sidewall of the upper collar 109 of the inner vessel 106.

As further illustrated by FIG. 2, the inner vessel 106 includes a reagent retention chamber 107 in fluid communication with the reagent chamber 111. The inner vessel 106 defines fluid vents 130, through which reagent may be transferred from the reagent chamber 111 to the sample collection chamber 103. However, in FIG. 2, any reagent within the reagent chamber 111 would be retained, owing to the closed configuration of the selectively movable sleeve valve 104. That is, as illustrated in FIG. 2, the fluid vents 130 are obstructed by an outer sleeve 108 of the selectively movable sleeve valve 104. An interior sidewall 122 of the outer sleeve 108 defines an aperture into which the inner vessel 106 extends, and the interaction between the interior sidewall 122 of the outer sleeve 108 and the exterior sidewall 118 of the inner vessel 106 creates a fluid tight connection—at least at and/or around fluid vents 130. The fluid tight connection between the outer sleeve 108 and the inner vessel 106 prevents the reagents within the reagent chamber 111 from passing into the reagent retention chamber 107 and out through fluid vents 130.

As also shown in FIG. 2, the outer sleeve 108 associates with sealing cap 110 and the opening of the sample collection chamber 103. A guide member 120 of the outer sleeve 108 protrudes away from the body of the outer sleeve 108 and extends into a guide channel 116 formed by the interior surface of the sealing cap 110. The guide member 120 acts, in some embodiments, to retain the outer sleeve 108 in association with the solution cap 110. The outer sleeve 108 additionally includes a lower collar 132 that associates with the interior sidewall of the sample collection chamber 103. In some embodiments, the lower collar 132 associates with the sample collection chamber 103 via an interference fit, which can serve to stabilize the selectively movable sleeve valve 104, the sealing cap 110, and the sample collection vessel 102. In some embodiments, the interference fit between the outer sleeve 108 and the sample collection chamber 103 is a liquid-tight fit.

As the complementary threads 124, 126 between the sealing cap 110 and the sample collection vessel 102 are inter-engaged and the sealing cap 110 is advanced towards the sample collection vessel 102, the inner vessel 106—which is coupled to the sample collection vessel 102—is similarly advanced. As shown in FIG. 3, the inner vessel 106 is pushed through the aperture defined by the outer sleeve 108, positioning the selectively movable sleeve valve 104 in an open configuration. In the open configuration depicted in FIG. 3, the fluid vents 130 are positioned below—and now unobstructed by—the lower terminal edge of the outer sleeve 108. Reagent(s) within the reagent chamber 103 can now freely pass through the reagent retention chamber 107 of the inner vessel 106, through the fluid vents 130, and into the sample collection chamber 103.

In the embodiment shown in FIG. 3, the outer sleeve 108 does not move relative to the sample collection vessel 102. The sealing cap 110 and the associated inner vessel 106 advance relative to the outer sleeve 108 and the sample collection vessel 102. In some embodiments, and as shown in FIG. 3, the body of the outer sleeve 108 above the lower collar 132 has a larger diameter than the lower collar 132, and this larger diameter body does not fit within the opening of the sample collection chamber 103. Instead, it abuts and is impeded by the upper rim of the sample collection chamber 103 that defines the opening thereof. This prevents the outer sleeve 108 from advancing along with the inner vessel 106 and the solution cap 110 toward sample collection vessel 102. The resistive force impeding progress of the outer sleeve 108 is greater than the frictional force between the inner vessel 106 and the outer sleeve 108, and the torque (or other force) applied to the solution cap 110 to associate the solution cap 110 with the sample collection vessel 102 is greater than the frictional force between the inner vessel 106 and the outer sleeve 108. Accordingly, the selectively movable sleeve valve 104 undergoes a conformational change where the inner vessel 106 advances through the outer sleeve 108, revealing the fluid vents 130 (as shown in FIG. 3).

As shown in FIGS. 2 and 3, the guide member 120 moves along the guide channel 116 as the solution cap 110 threadedly secures to the sample collection vessel 102.

In some embodiments, the distance required to open the selectively movable sleeve valve 104 is proportional to the distance required to at least partially unobstruct the fluid vents 130. This distance may be the same or less than the distance between the terminal edge of the solution cap 110 and the stop member 128 disposed on the external surface of the sample collection vessel 102 when the connection members 124, 126 thereof initially engage.

Although there are only two fluid vents 130 illustrated in FIGS. 2 and 3, it should be appreciated that in some embodiments there can be more or fewer fluid vents. For example, a second pair of fluid vents 130 (not shown) can be defined on the opposite side of the inner vessel 106. In some embodiments, the fluid vents can be a different shape and/or the selectively movable sleeve valve 104 may operate differently than illustrated in FIGS. 2 and 3. For example, the outer sleeve may define an open-ended chamber into which the inner vessel is inserted. However, instead of being pushed through an open bottom of the outer sleeve, depression of the inner vessel (e.g., by association of the sealing cap with the sample collection vessel) can align fluid vents defined by the inner vessel with analogous fluid vents defined by the outer sleeve, thereby providing a through hole between the sample collection chamber, the reagent retention chamber of the inner vessel, and the reagent chamber of the solution cap.

Figure 4:
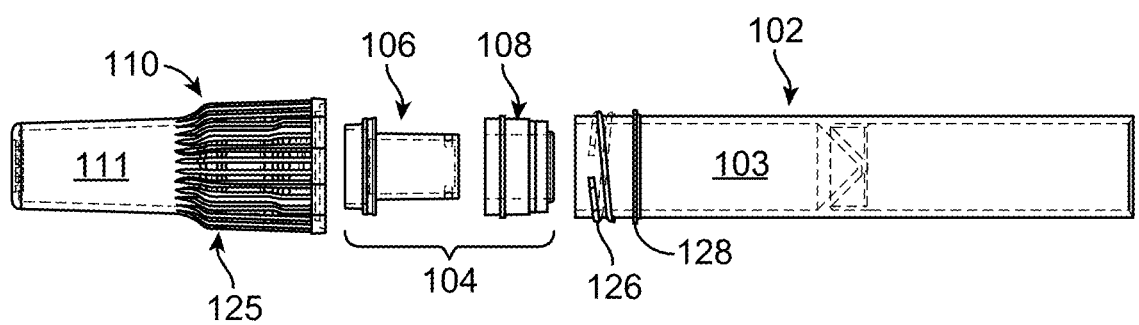
FIG. 4 illustrates an exploded elevation view of a sample collection system similar to the three-dimensional model depicted in FIG. 1 that includes a cap configured to receive a selectively movable sleeve valve.

Referring now to FIG. 4, the sealing cap 110 may additionally include a plurality of external ridges 125. The external ridges 125 can facilitate a user to better grip the sealing cap 110 while positioning the cap 110 over the sample collection vessel 102. Additionally, or alternatively, the external ridges 125 can be used to rotate and close the sealing cap 110 onto sample collection vessel 102. In some embodiments, ridges 125 may beneficially enable the user to more forcefully torque the sealing cap 110, and the external ridges 125 can provide the user with a better grip during that process. Ridges 125 can also facilitate retraction and/or closure of the selectively movable sleeve valve 104 and/or removal of the sealing cap 110 at the laboratory when accessing the biological sample, such as manually or by an automated removal mechanism.

Figure 5:
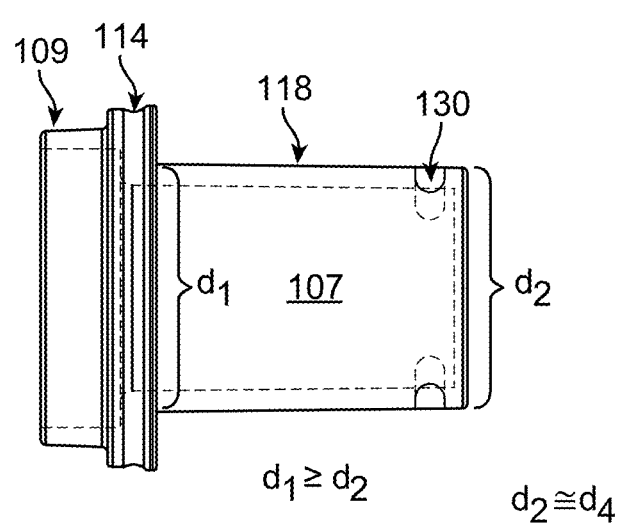
FIG. 5 illustrates an elevation view of the inner vessel of the sample collection system depicted in FIG. 4.

Referring now to FIG. 5, the inner vessel 106 includes one or more tapered regions, which can, among other things, help fit the inner vessel 106 into the solution cap 110 and into the aperture 134 of the outer sleeve 108. For example, the inner vessel 106 can include an upper collar 109 that is sized and shaped to fit within the sample collection chamber 103 and to create a fluid tight seal therewith (as described above). As shown, the upper collar 109 can be tapered with a larger diameter adjacent the retaining ring 114 and a smaller diameter moving away from the retaining ring 114 toward the terminal end thereof. The smaller diameter end of the upper collar 109 can be a smaller diameter than the diameter of the reagent chamber 111, which can beneficially allow the inner vessel 106 to be more easily associated with the solution cap 102. As the diameter of the upper collar 109 increases, it forms an interference fit with the associated reagent chamber 111, which can additionally be a fluid-tight fit.

The inner vessel 106 additionally includes a tapered exterior sidewall 118 that is sized and shaped to fit within the aperture 134 of the outer sleeve 108. As illustrated, the exterior sidewall 118 can taper from a first diameter d1 to a second diameter d2, where d1>d2.

Figure 6:
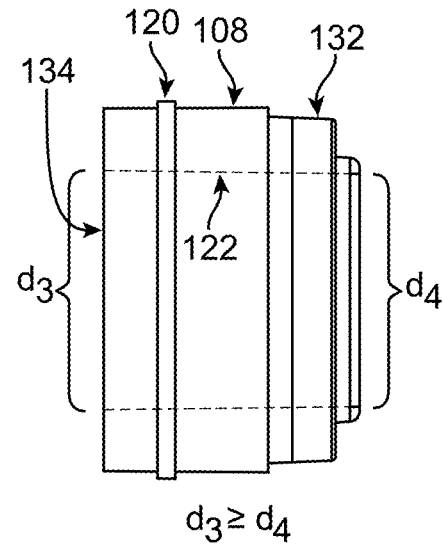
FIG. 6 illustrates an elevation view of the outer sleeve of the sample collection system depicted in FIG. 4.

As shown in FIG. 6, the interior sidewall defining the aperture 134 of the outer sleeve 108 can additionally be tapered. For example, as shown in FIG. 6, the sidewall 122 can be tapered from a proximate end having a diameter d3 to a distal end having a diameter d4, where d3>d4. The distal end diameter d4 can be, in some embodiments, about the same size as the second diameter d2 of the inner vessel 106 such that when the inner vessel 106 is associated with the outer sleeve 108, an interference fit is created, which can additionally be a fluid-tight fit.

In some embodiments, the exterior sidewall 118 of the inner vessel 106 is tapered to the same degree as the interior sidewall 122 of the outer sleeve 108. In such an embodiment, the interior sidewall 122 may associate directly with the exterior sidewall 118 along its entire length and forming an interference fit therebetween.

In some embodiments, the exterior sidewall 118 of the inner vessel 106 is tapered to a different degree than the interior sidewall 122 of the outer sleeve 108. For example, the interior sidewall 122 can be tapered more aggressively than the exterior sidewall 118 such that d1<d3. In such an embodiment, a gap would form between the outer sleeve 108 and the inner vessel 106 at the proximate end of the outer sleeve 108. In some embodiments, the length of the aperture 134 a shorter than the length of the exterior sidewall 118, and only a portion of the exterior sidewall 118 associates with the aperture 134. Accordingly, d1 may be roughly equivalent to d3, and the degree of taper of the exterior sidewall 118 would still be less than the degree of taper of the interior sidewall 122 defining aperture 134. In such an embodiment, a gap would form between the outer sleeve 108 and the inner vessel 106 at the proximate end of the outer sleeve 108, similar to that described above.

As shown in FIGS. 2 and 3, the selectively movable sleeve valve 104 can be configured in a closed configuration (FIG. 2) and an open configuration (FIG. 3). In the open configuration illustrated in FIG. 3, the inner vessel 106 protrudes through the outer sleeve 108. As discussed above with respect to FIGS. 5 and 6, this causes a region of the inner vessel 106 having a larger diameter than d2 and/or d4 to be associated with the distal end of the outer sleeve 108 (e.g., the region associated with d4). In some embodiments, the outer sleeve 108 can be made of a material configured to flex under such strain, allowing the larger diameter portion to extend, as shown in FIG. 3. For example, the outer sleeve may be made of polypropylene or a thermoplastic elastomer. The properties of the material should allow for a fluid tight connection between the inner vessel 106 and the outer sleeve 108 also allow the selectively movable sleeve valve 104 moved between open closed configurations.

In some embodiments, when the inner vessel 106 protrudes through the outer sleeve 108, causing the outer sleeve 108 to elastically flex (e.g., when the selectively movable sleeve valve 104 is in an open configuration), the tapered nature of the exterior sidewall 118 and the interior sidewall 122 defining the aperture 134 can cause the selectively movable sleeve valve 104 to return to a closed configuration (as shown in FIG. 2) when whatever force that is being applied to cause the open configuration is relieved (e.g., the sealing cap 100 is loosened). Upon relief of the force causing the open configuration, the elastically flexed outer sleeve 108 can provide sufficient force to move inner vessel 106 back through the aperture 134.

Accordingly, in some embodiments, tightening the association of the solution cap 110 with the sample collection vessel 102 forces the selectively movable sleeve valve 104 into an open configuration where the outer sleeve 108 is elastically flexed, and loosening the association of the solution cap 110 with the sample collection vessel 102 allows the outer sleeve 108 to return to a less flexed state, pushing the inner vessel 106 back into the aperture 134, obstructing fluid vents 130, and returning the selectively movable sleeve valve 104 to a closed configuration.

As shown in FIG. 7, some embodiments of the present disclosure include a sample collection system 200 having a sample collection vessel 202, a sleeve valve 204 that can be selectively and reversibly unsealed and resealed and which comprises an outer sleeve 208 and an inner vessel 106, and a solution cap 110 operable to cover and seal the opening of the sample collection vessel 202. The outer sleeve 208 can include a detent 207 that mates with or otherwise selectively associates with a ring structure 205 disposed on an interior sidewall 203 of the sample collection vessel 202. When assembled, the detent-ring association can enable or assist the sleeve valve device 204 in being selectively and, if desired, reiteratively unsealed and resealed.

Methods Implementing a Solution Cap Having a Selectively Movable Sleeve Arm

With continued reference to FIGS. 1-6, an exemplary method for implementing a multi-part sample collection kit, as described above, includes receiving a biological sample through a funnel connected to the sample collection vessel 102. The received biological sample can enter directly into the sample collection vessel 102 or by gravitational flow along an interior funnel sidewall. The method can additionally include removing the funnel from the sample collection vessel 102 after facilitating receipt of the biological sample, and associating a sealing cap 110 with the sample collection vessel 102. The method can additionally include securing the sealing cap 110 (e.g., by rotating the sealing cap 110 along complementary threads between the cap 110 and the vial 102) to close the cap 110 over the top of the sample collection vessel 102. The sealing cap 110 can contain preservation reagent(s) that are released as the sealing cap 110 is rotated and closed over the sample collection vessel 102. In some embodiments, a selectively movable sleeve valve 104 associated with the sealing cap 110 undergoes a conformational change when the sealing cap 110 is rotated and closed over the collection vial 102.

As shown in FIGS. 2 and 3, the solution cap 110 secures to and seals the collection vessel 102 and can do so by any means described herein or as known in the art. In this closed and sealed state, the selectively movable sleeve valve 104 is in an open configuration, and the reagent(s) mix with the collected sample. The collection vessel 102 can be shaken to allow all or at least most of the preservation reagent to cover the collected sample. Additionally, the biological sample therewithin is beneficially protected from the outside atmosphere by being air- and water-tight. This reduces the chances of the sample contamination and helps maintain the integrity of the probative component during transportation to the laboratory.

In some embodiments, the solution cap is under pressure and moving the selectively movable sleeve valve into an open position causes the preservation reagent(s) stored within the solution cap to be forcefully expelled into the sample collection chamber. This can beneficially encourage stored reagent(s) to mix with the collected sample and may additionally act to preserve the reagent(s) and/or the probative component thereof.

Methods can additionally include removing the preserved sample from the sample collection system. This can involve, for example, the steps of unscrewing or otherwise removing the solution cap from the sample collection vessel. In doing so, the outer sleeve can be retained by the sample collection vessel while the solution cap and associated inner vessel are drawn away from the sample collection vessel. This can cause the sleeve valve to reseal (e.g., return to a closed configuration). Further disassociation of the solution cap from the sample collection vessel can cause the sleeve valve to be removed in a resealed state, exposing the opening of the sample collection vessel and allowing access to the preserved biological sample.

Referring now to FIGS. 8 and 9, an exemplary use of a sample collection system 200 can include a sealable and/or resealable sleeve valve 204. For example, during assembly of the solution cap 110 with the associated sleeve valve 204, the reagent reservoir 111 of the solution cap can be filled with a measure of sample preservation reagent(s). The inner vessel 106 of the sleeve valve 204 can then be press-fit into and retained by the solution cap 110. As shown in FIGS. 8 and 9, the inner vessel 106 defines a reagent chamber 107 that is in fluid communication with the reagent reservoir 111 of the solution cap 110 and further defines a plurality of fluid vents 130 through which reagent within the reagent reservoir can be delivered to a collected sample. An upper collar 109 of the inner vessel 106 extends into—and provides an interference fit with—the reagent reservoir 111 of the solution cap 110, and a retaining channel defined by the inner vessel receives a complementary protrusion from the solution cap sidewall, further anchoring the inner vessel 106 within the solution cap 110 to prevent separation. Together (or individually) these components of the inner vessel 106 can act to provide a fluid-tight seal between the inner vessel 106 and the solution cap 110.

In the exemplified embodiment, the combination of inner vessel 106 and outer sleeve 208 comprises the sleeve valve 204, which can be selectively and reversibly moved between a sealed configuration 200A and an unsealed configuration 200B. When the outer sleeve 208 is associated with the inner vessel 106 in the sealed configuration 200A, it can prevent the premature or unintentional expulsion of reagent from the solution cap 110.

Assembly of the sleeve valve 204 can occur before, during, or after the inner vessel 106 is attached to the solution cap 110. It can involve advancing the outer sleeve 208 over the inner vessel 106 and within the solution cap 110 until an exterior-facing guide member 220 on the outer sleeve is received (e.g., snap-fittedly received) into a guide channel 116 of the solution cap 110. Once the outer sleeve 208 has been advanced over the inner vessel 106 and the guide member 220 received within the guide channel 116 of the solution cap 110, the outer sleeve 106 is in an initially sealed configuration 200A, thereby covering the fluid vents 130 of the inner vessel 106 and sealing and retaining the sample preservation reagent(s) inside the solution cap 110 and inner vessel 106 (e.g., as illustrated in FIG. 2 but before the solution cap has been placed onto the sample collection vessel).

The guide channel 116 of the solution cap 110 can be sized to allow limited translational movement of the guide member 220 within the guide channel 116. This, in turn, restricts the movement of the inner vessel 106 relative to the outer sleeve 208 when the solution cap 110 is secured and unsecured from the sample collection vessel 202 (e.g., as illustrated in FIGS. 8 and 9 when the solution cap 110 is secured to the sample collection vessel 202, causing the selective unsealing of the sleeve valve 204). An inner facing edge or protrusion of the solution cap 110 can define a lower end of the guide channel 116 and can act to retain the guide member 220 within the guide channel 116, preventing separation of the outer sleeve 208 from the solution cap 110 when the solution cap 110 is decoupled from the sample collection vessel 202.

In an exemplary use, the sample collection vessel 202 is used to receive a biological sample through the opening of and into the sample collection vessel 202 (e.g., receiving saliva through an optional funnel temporarily attached to the sample collection vessel 202). After the biological sample is received within the sample collection vessel 202, the user can place the solution cap 110 over the sample collection vessel 202, with the sleeve valve 204 facing the opening of the sample collection vessel 202 and advance the sleeve valve 204 into the opening of the sample collection vessel 202. When the sleeve valve 204 is advanced through the opening of the sample collection vessel 202, a detent 207 formed within the lower collar of the outer sleeve 208 can mechanically engage a protruding retention ring 205 on the interior sidewall 203 of the sample collection vessel 202. The ring-detent engagement can prevent the sleeve 204 from being pushed farther into the sample collection vessel 202, but in some variations, the body 211 of the outer sleeve 208 above the lower collar abuts an upper rim 213 of the sample collection vessel 202, thereby preventing the sleeve 204 from being pushed any farther into the sample collection vessel 202.

Further advancement of the solution cap 110 toward the sample collection vessel 202, including engagement of complementary interlocking threads located on the solution cap 110 and the sample collection vessel 202, can force the inner vessel 106 through the outer sleeve 208 and affect a conformational change in the sleeve valve 204 from the sealed position 200A shown in FIG. 8 to the unsealed position 200B shown in FIG. 9. Moving the sleeve valve 204 from the sealed position 200A to the unsealed position 200B un-occludes the fluid vents 130 and allows the reagent(s) to flow into the sample collection vessel 202.

The foregoing unsealing of the sleeve valve can be temporary and reversible. For example, when the solution cap 110 is removed from the sample collection vessel 202 to recover the biological sample, the sleeve valve 204 can be restored to the sealed configuration 200A, reestablishing the seal between the outer sleeve 208 and inner vessel 106. As the solution cap 110 is unscrewed from the sample collection vessel 202, in some embodiments, the outer sleeve 208 can be temporarily retained in a fixed position within the sample collection chamber while the inner vessel 106 is withdrawn, causing the outer sleeve 208 to re-occlude the fluid vents 130 (e.g., moving the sleeve valve 204 from the unsealed configuration 200B of FIG. 9 to the resealed configuration 200A of FIG. 8). The outer sleeve 209 can be temporarily retained in the fixed position due to the retention ring 205 within the sample collection vessel 202 mechanically engaging with the detent 207 on the lower collar of the outer sleeve 208. The frictional forces between the outer sleeve 208 and inner vessel 106 can be less than the force required to disengage the ring-detent interaction, allowing such relative movement.

When the inner vessel 106 has been withdrawn relative to the outer sleeve 208 so as to reseal the fluid vents 130, the guide member 220 can reach the end of the guide channel 116 where further movement is impeded by the inner facing edge or protrusion of the solution cap 110. The sample collection system 200 is designed in some embodiments so that the solution cap 110 and sleeve valve 204 can—at this point—be removed from the sample collection vessel 202 without the catastrophic failure of any components. That is, the sample collection system 200 can be designed so that the detent 207 on the outer sleeve 208 can be disengaged from the protruding ring 205 of the sample collection vessel 202 while maintaining the integrity of the solution cap-sleeve valve association. This can be enabled, for example, by engineering the components such that the mechanical force required to disengage the ring 205 and detent 207 is less than the force required to remove the guide member 220 from the guide channel 116. Further withdrawal of the solution cap 110 from the sample collection vessel can, therefore, overcome the ring-detent interaction, permitting the solution cap 110, inner vessel 106, and outer sleeve 208 to be removed as a single unit from the sample collection vessel 202—with the valve 204 in the resealed configuration 200A.

It should be appreciated that although the foregoing embodiment depicted the ring 205 being associated with the sample collection vessel 202 and the detent 207 being associated with the outer sleeve 208, in some embodiments, the attachment mechanism between the two components may be switched or replaced by other complementary components that perform the same or similar function. For example, the sample collection vessel may include a detent within an interior sidewall that associates with a ring structure disposed on the outer sleeve.

Figure 10:
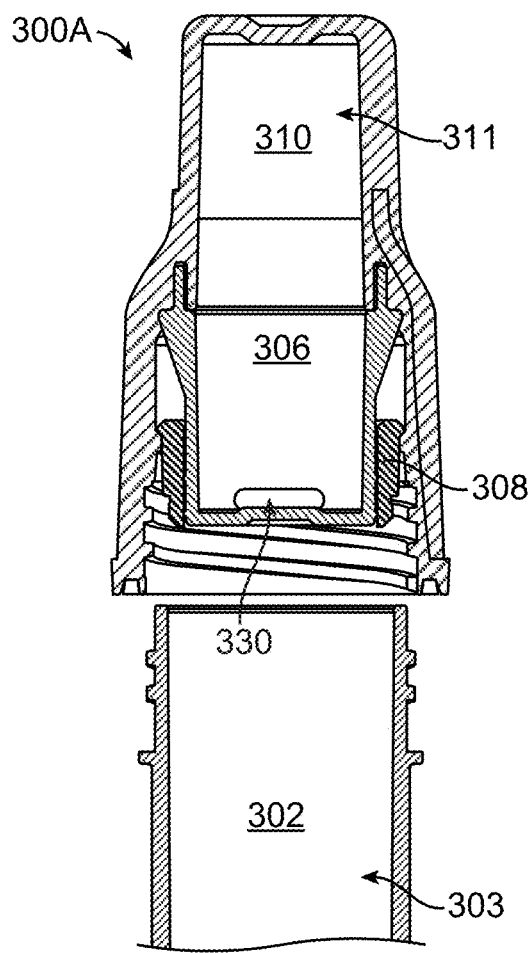
FIG. 10 illustrates a cross-sectional, unassembled view of a sample collection system with a selectively movable sleeve valve depicted in an unsealed configuration.
Figure 11:
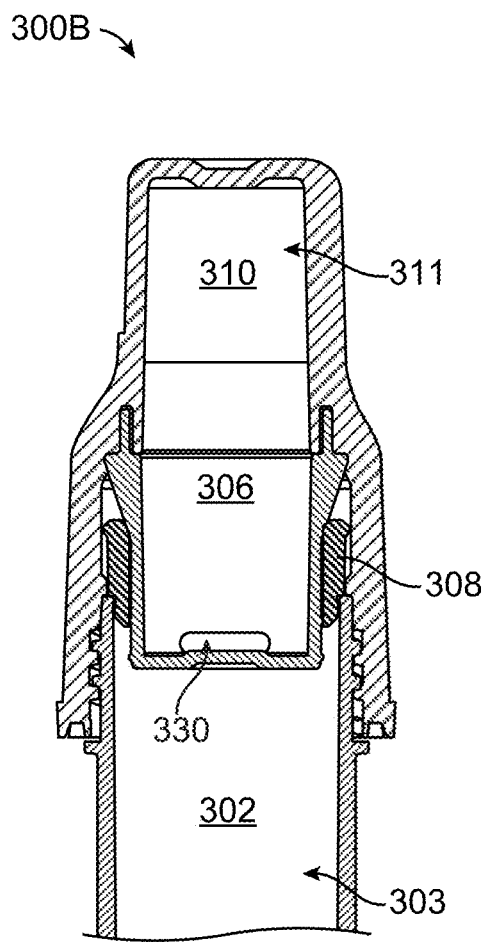
FIG. 11 illustrates a cross-sectional, assembled view of a sample collection system with the selectively movable sleeve valve depicted in a sealed/resealed configuration.

FIGS. 10 and 11 illustrate a cross-sectional, unassembled view 300A and a cross-sectional, assembled view 300B, respectively, of an additional embodiment of a sample collection system 300 with a selectively movable sleeve valve 304 depicted in an unsealed configuration and in a sealed/resealed configuration, respectively.

Similar to the embodiments of FIGS. 1-9, the system 300 includes a collection vessel 302 and optionally, a funnel (not shown), which can be associated with a top portion of the collection vessel 302 and in fluid communication with a sample collection chamber 303 of the collection vessel 302. The biological sample collection system 300 can also include the selectively movable sleeve valve 304 comprised of an inner vessel 306 and an outer sleeve 308 associated with a sealing cap 310 that has a reagent chamber 311 disposed within or integrated with the sealing cap 310. The sealing cap 310—together with the selectively movable sleeve valve 304—can be sized and shaped to associate with a top portion of the collection vial 302, fitting over and sealing an opening of the sample collection chamber 303. For the sake of clarity, the description for corresponding components of the systems 100 and 200 applies to the system 300 and is incorporated herein.

Figure 12:
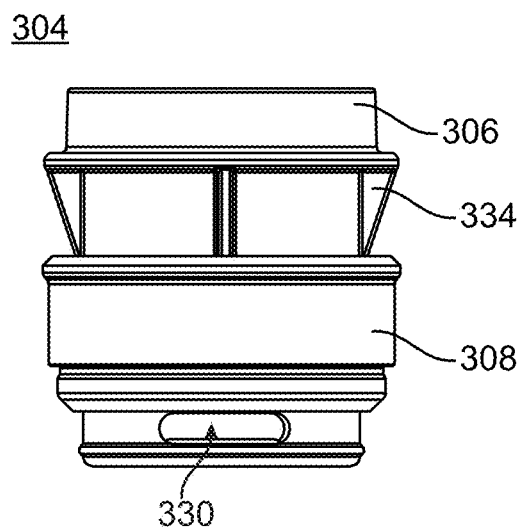
FIG. 12 illustrates the selectively movable sleeve valve of FIGS. 10-11.

In the exemplified embodiment, the combination of inner vessel 306 and outer sleeve 308 comprises the sleeve valve 304, as shown in FIG. 12. The sleeve valve 304 can be selectively and reversibly moved between the sealed configuration 300A and the unsealed configuration 300B. When the outer sleeve 308 is associated with the inner vessel 306 in the sealed configuration 300A, it can prevent the premature or unintentional expulsion of reagent from the solution cap 110 through the fluid vent 330. In the embodiments of FIGS. 10-12, the outer sleeve 308 encircles a bottom portion of the inner vessel 306 where the fluid vent 330 is positioned. The inner vessel 306 comprises a plurality of ribs 334 about an upper portion of the inner vessel 306. The plurality of ribs 334 may be spaced evenly or at varying intervals about the outer surface of the inner vessel 306.

After a biological sample is received within the sample collection vessel 302, the user can place the solution cap 310 over the sample collection vessel 302, with the sleeve valve 304 facing the opening of the sample collection vessel 302 and advance the sleeve valve 304 into the opening of the sample collection vessel 302. When the sleeve valve 304 is advanced through the opening of the sample collection vessel 302 toward the sample collection vessel 302, including engagement of complementary interlocking threads located on the solution cap 310 and the sample collection vessel 302, it can force the inner vessel 306 through the outer sleeve 308 and affect a conformational change in the sleeve valve 304 from the sealed position 300A shown in FIG. 10 to the unsealed position 300B shown in FIG. 11. The outer sleeve 308 is moved towards the plurality of ribs 334. Moving the sleeve valve 304 from the sealed position 300A to the unsealed position 300B un-occludes the fluid vents 330 and allows the reagent(s) to flow into the sample collection vessel 302.

Figure 13A:
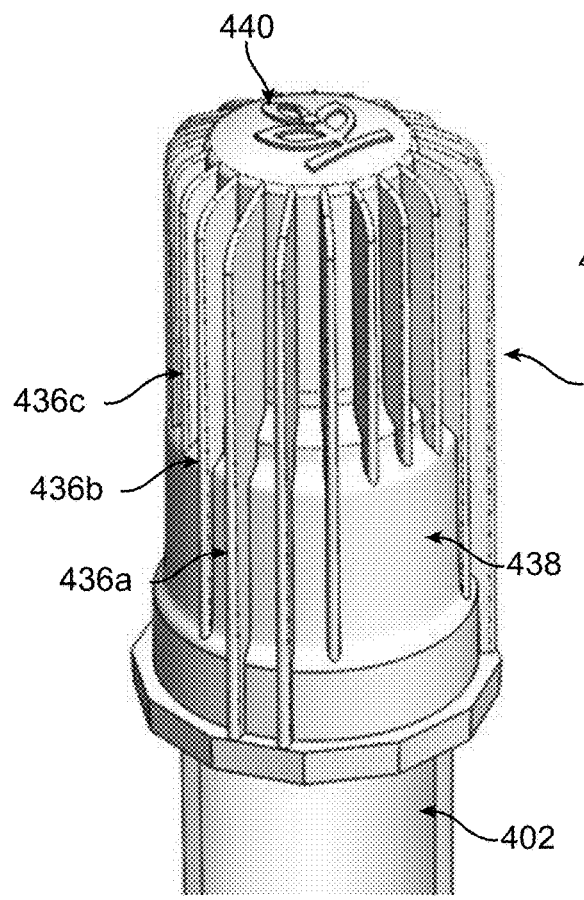
FIGS. 13A-13C illustrate perspective views of a sealing cap.
Figure 13B:
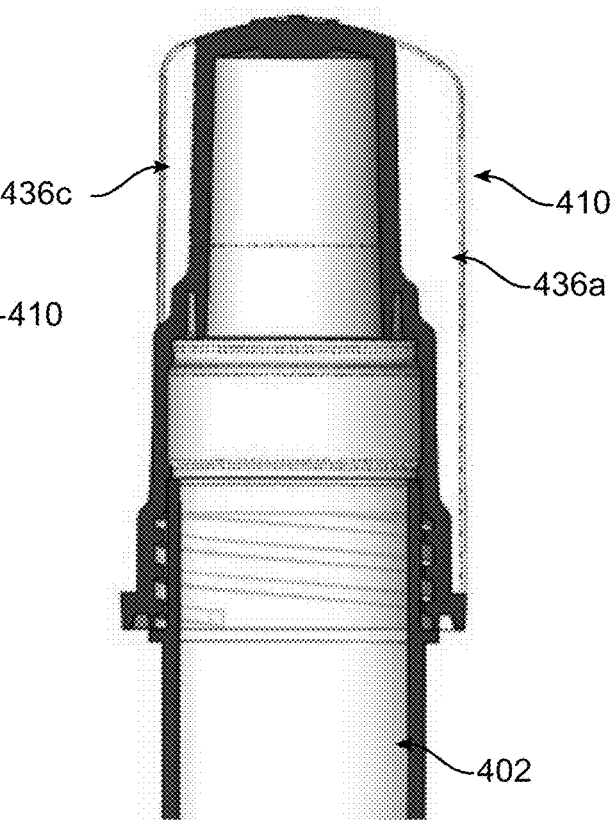
Figure 13C:
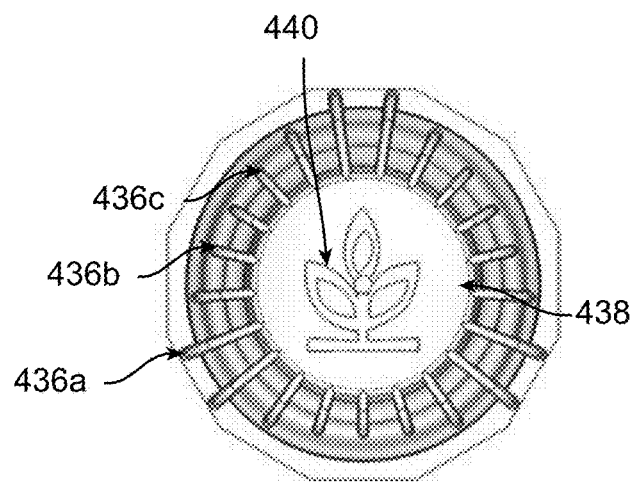

FIGS. 13A-13C illustrate a perspective view, a cross-sectional view, and a top view of a sealing cap 410. The design of a sealing cap may have various functional features, for example that enable a user to conveniently and reliably associate the sealing cap and the sample collection vessel, and various aesthetic features, such as a brand or logo. As described with regard to the embodiments of FIGS. 1-9, applying a rotational force threadedly associates the sealing cap 410 and the sample collection vessel 402, and applying a directionally opposite rotation force disassociates the sealing cap and the sample collection vessel. In the embodiments of FIGS. 13A-13C, the sealing cap 410 comprises a plurality of gripping features 436 about an outer surface 438 and a logo 440. The plurality of gripping features 436 enable a user to grip the sealing cap to apply a rotational force to associate and disassociate the sealing cap with the sample collection vessel. While the geometry of the outer surface 438 may vary, the sealing cap generally has a cylindrical core. The plurality of gripping features 436 may vary in shape, length, arrangement, and orientation.

As illustrated in FIGS. 13A-13C, the outer surface 438 has a cylindrical core with three portions, each having different diameters. The gripping features 436 are elongated ribs that are equally and radially spaced about the outer surface 438. A length of each gripping feature 436 may vary; FIG. 13A illustrates a plurality of long ribs 436a, medium ribs 436b, and short ribs 436c, corresponding to the differing diameters of the outer surface 438. The gripping features 436 are arranged in a pattern, but in other embodiments they may be arranged differently (e.g., at varying intervals). As shown in the top view in FIG. 13C, a height of each gripping feature 436 (in a perpendicular direction relative to the outer surface 438) may also vary. FIG. 13C illustrates the plurality of gripping features 436 forming approximately a triangular shape about the outer surface 438, where a height of each gripping feature 436 corresponds to a length of each gripping feature 436. In other words, the gripping features 436 with the longest length are the tallest in height, 440 the gripping features 436 with the shortest length are the shortest in height. FIG. 13C illustrates the logo 440 positioned on the outer surface 438 in the center of the radially spaced gripping features 436.

FIGS. 14A-14N illustrate perspective views of various embodiments of a sealing cap. As previously described, the design of a sealing cap may have various functional features, for example that enable a user to conveniently and reliably associate the sealing cap and the sample collection vessel, and various aesthetic features, such as a brand or logo. While the geometry of the outer surface of the sealing cap may vary, the sealing cap generally has a cylindrical core. The gripping features on the outer surface may vary in shape, length, arrangement, and orientation, or similar.

FIG. 14A illustrates an embodiment of a sealing cap 1400 that includes an outer surface and a plurality of gripping features. In the embodiment of FIG. 14A, the outer surface is substantially cone-shaped, and the plurality of gripping features are elongated ribs that are radially and equally spaced about the outer surface. The elongated ribs extend from a top edge of the sealing cap 1400 to a bottom edge of the sealing cap 1400. Two gripping features that are positioned opposite each other protrude a greater distance from the outer surface than the remaining gripping features, creating two "wings" for gripping the sealing cap 1400.

FIG. 14B illustrates an embodiment of a sealing cap 1402 that includes an outer surface and a plurality of gripping features. In the embodiment of FIG. 14B, the outer surface is substantially cone-shaped, and the plurality of gripping features are angled loops that protrude from a bottom portion of the sealing cap 1402. The plurality of gripping features are radially and equally spaced about the outer surface.

FIG. 14C illustrates an embodiment of a sealing cap 1404 that includes an outer surface and a plurality of gripping features. In the embodiment of FIG. 14C, the outer surface is substantially cylindrical with a rounded top edge, and the plurality of gripping features are elongated ribs that are radially and equally spaced about the outer surface. The elongated ribs extend from the top edge of the sealing cap 1404 to about the middle of the sealing cap 1404, covering an upper portion of the sealing cap 1404. On a bottom portion of the sealing cap 1404, the outer surface is smooth and includes a logo.

FIG. 14D illustrates an embodiment of a sealing cap 1406 that includes an outer surface and a plurality of gripping features. In the embodiment of FIG. 14D, the outer surface is about cone-shaped with a rounded top edge, and the plurality of gripping features are elongated ribs that are radially and equally spaced about the outer surface. The elongated ribs extend from the top edge of the sealing cap 1406 to a bottom edge of the sealing cap 1406. The elongated ribs protrude from the outer surface such that the elongated ribs create a substantially cylindrical boundary. On a top portion of the sealing cap 1404, the outer surface includes a logo.

FIG. 14E illustrates an embodiment of a sealing cap 1408 that includes an outer surface and a plurality of gripping features. In the embodiment of FIG. 14E, the outer surface is substantially cylindrical, and the plurality of gripping features are loops that are arranged similar to a flower petal shape. In between the corner loops are elongated ribs. The loops and the elongated ribs extend from the top edge of the sealing cap 1408 to the bottom edge of the sealing cap 1408. On one or more of the loops is a logo.

FIG. 14F illustrates an embodiment of a sealing cap 1410 that includes an outer surface and a plurality of gripping features. In the embodiment of FIG. 14F, the outer surface is substantially cylindrical, and the plurality of gripping features are loops that are arranged similar to a flower petal shape. In between the corner loops are flat surfaces that bridge between the corner loops. The loops and the flat surfaces extend from the top edge of the sealing cap 1410 to the bottom edge of the sealing cap 1410. On one or more of the flat surfaces is a logo.

FIG. 14G illustrates an embodiment of a sealing cap 1412 that includes an outer surface and a plurality of gripping features. In the embodiment of FIG. 14G, the outer surface is substantially rectangular, and the plurality of gripping features are flat surfaces. The flat surfaces extend from near the top edge of the sealing cap 1412 to near the bottom edge of the sealing cap 1412. On top and on bottom of the flat surfaces, a plurality of short ribs extend from the top edge or the bottom edge to the flat surfaces. The short ribs are radially and equally spaced about the outer surface. On one or more of the flat surfaces is a logo.

FIG. 14H illustrates an embodiment of a sealing cap 1414 that includes an outer surface and a plurality of gripping features. In the embodiment of FIG. 14H, the outer surface is substantially rectangular, and the plurality of gripping features are elongated ribs that extend from a top edge of the sealing cap 1414 to a bottom edge of the sealing cap 1414. The elongated ribs are radially and equally spaced about the outer surface.

FIG. 14I illustrates an embodiment of a sealing cap 1416 that includes an outer surface and a plurality of gripping features. In the embodiment of FIG. 14I, the outer surface is substantially rectangular, and the plurality of gripping features are elongated ribs that extend from a top edge of the sealing cap 1416 to a bottom edge of the sealing cap 1416. The elongated ribs are radially and equally spaced about the outer surface. A flat surface extends perpendicularly across the elongated ribs about the outer surface, and on the flat surface is a logo. In the embodiment of FIG. 14I, the flat surface is positioned near a bottom edge of the sealing cap 1416.

FIG. 14J illustrates an embodiment of a sealing cap 1418 that includes an outer surface and a plurality of gripping features. In the embodiment of FIG. 14J, the outer surface is substantially cylindrical, and the plurality of gripping features are loops that protrude from the outer surface. The loops form concave surfaces with adjacent loops, creating a boundary resembling a square with concave surfaces, and the loops extend from near a top edge of the sealing cap 1418 to near a bottom edge of the sealing cap 1418. Near the bottom edge, curved surfaces connect the loops to the bottom edge of the sealing cap 1418. At the top edge, the outer surface is exposed within the loops.

FIG. 14K illustrates an embodiment of a sealing cap 1420 that includes an outer surface and a plurality of gripping features. In the embodiment of FIG. 14K, the outer surface is substantially cylindrical, and the plurality of gripping features are loops that protrude from the outer surface. The loops form concave surfaces with adjacent loops, creating a boundary resembling a triangle with rounded corners and concave surfaces between the corners, and the loops extend from near a top edge of the sealing cap 1418 to a bottom edge of the sealing cap 1418. At the top edge, the outer surface is exposed within the loops. One of the concave surfaces includes a logo.

FIG. 14L illustrates an embodiment of a sealing cap 1422 that includes an outer surface and a plurality of gripping features. In the embodiment of FIG. 14L, the outer surface is substantially cylindrical, and the plurality of gripping features are loops that protrude from the outer surface. The loops are flat surfaces, where the loops alternate in size between large and small, creating a boundary resembling a triangle flat corners, and the loops extend from a top edge of the sealing cap 1422 to a bottom edge of the sealing cap 1422. At the top edge, the outer surface is exposed within the loops. One or more of the flat surfaces includes a logo.

FIG. 14M illustrates an embodiment of a sealing cap 1424 that includes an outer surface and a plurality of gripping features. In the embodiment of FIG. 14M, the outer surface is substantially cylindrical, and the plurality of gripping features are elongated ribs that protrude from the outer surface. The elongated ribs create a boundary resembling a triangle flat corners, where the flat corners are formed by loops protruding from the outer surface. The gripping features extend from a top edge of the sealing cap 1424 to a bottom edge of the sealing cap 1424. At the top edge, the outer surface is exposed within the loops. One or more of the loops includes a logo.

FIG. 14N illustrates an embodiment of a sealing cap 1426 that includes an outer surface and a plurality of gripping features. In the embodiment of FIG. 14N, the outer surface is substantially cylindrical, and the plurality of gripping features are loops that protrude from the outer surface. The loops are flat surfaces, where the loops alternate in size between large and small, creating a boundary resembling a triangle flat corners, and the loops extend from a top edge of the sealing cap 1426 to a bottom edge of the sealing cap 1426. On the larger flat surfaces, a plurality of elongated ribs extend along the flat surface. At the top edge, the outer surface is exposed within the loops. One or more of the corner loops includes a logo.

Unless defined otherwise, all technical and scientific terms used herein have the same meaning as commonly understood by one of ordinary skill in the art to which the present disclosure pertains.

It will also be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A biological sample collection system, the system comprising:
    a sample collection vessel, the sample collection vessel comprising a sample collection chamber, an interior sidewall and an opening configured to receive a biological sample into the sample collection chamber, the opening being defined by a rim of the sample collection vessel and the rim having an inner diameter;
    a sealing cap securable to the sample collection vessel, the sealing cap comprising a reagent chamber and carrying a sleeve valve, the reagent chamber configured to store a reagent therein, the sleeve valve having a closed configuration and an open configuration, the sleeve valve comprising:
        an inner vessel comprising a fluid vent, the inner vessel in fluid communication with the reagent chamber of the sealing cap, and
        an outer sleeve surrounding the inner vessel and forming a fluid-tight fit with the inner vessel, the outer sleeve comprising a first section and a second section, the first section having a first diameter larger than the inner diameter and the second section having a second diameter equal to or smaller than the inner diameter;
    wherein, in the closed configuration of the sleeve valve, the outer sleeve is positioned to obstruct the fluid vent,
    wherein the sleeve valve is configured to be movable to the open configuration in response to the sealing cap being secured to the sample collection vessel, and
    wherein, in the open configuration, the second section is in contact with the interior sidewall of the sample collection vessel and the first section of the outer sleeve is pushed by the rim of the sample collection vessel, thereby moving the outer sleeve relative to the inner vessel to reveal the fluid vent to allow the reagent to flow from the reagent chamber into the sample collection chamber, thereby dispensing the reagent into the sample collection chamber.

2. The biological sample collection system of claim 1, wherein the sample collection vessel further comprises a connection member.

3. The biological sample collection system of claim 2, wherein the sealing cap further comprises a complementary connection member configured to associate with the connection member of the sample collection vessel to secure the sealing cap to the sample collection vessel.

4. The biological sample collection system of claim 3, wherein the connection member and the complementary connection member each comprise threads.

5. The biological sample collection system of claim 4, wherein the threads of the complementary connection member comprise a plurality of internal threads of the sealing cap.

6. The biological sample collection system of claim 1, wherein the biological sample collection system comprises a separable two-piece sample collection system, the sample collection vessel comprising a first piece of the separable two-piece sample collection system, and the sealing cap comprising a second piece of the separable two-piece sample collection system.

7. The biological sample collection system of claim 1, wherein an interior sidewall of the outer sleeve defines an aperture configured to accommodate at least a portion of the inner vessel.

8. The biological sample collection system of claim 1, wherein the inner vessel comprises a retaining ring configured to associate with a protrusion disposed within an interior portion of the sealing cap.

9. The biological sample collection system of claim 8, wherein an association of the retaining ring and the protrusion creates a fluid-tight connection between the inner vessel and the sealing cap.

10. The biological sample collection system of claim 8, wherein the inner vessel additionally comprises a reagent retention chamber, and wherein the reagent retention chamber is in fluid communication with the reagent chamber of the sealing cap when the retaining ring of the inner vessel is associated with the protrusion of the sealing cap.

11. The biological sample collection system of claim 1, wherein the outer sleeve comprises a guide member, and wherein the guide member is configured to be received by a guide channel of the sealing cap.

12. The biological sample collection system of claim 1, wherein the second section of the outer sleeve corresponds to a lower collar that is configured to create a fluid-tight seal between the outer sleeve and the opening of the sample collection chamber when the sealing cap is secured to the sample collection vessel.

13. The biological sample collection system of claim 7, wherein the inner vessel is tapered between a proximal end of the inner vessel and a distal end of the inner vessel, the proximal end of the inner vessel having a first proximal end diameter and the distal end of the inner vessel having a second distal end diameter, and wherein the aperture defined by the interior sidewall of the outer sleeve is tapered between a proximal end of the outer sleeve and a distal end of the outer sleeve, the proximal end of the outer sleeve having a third proximal end diameter and the distal end of the outer sleeve having a fourth distal end diameter.

14. The biological sample collection system of claim 13, wherein the first proximal end diameter is greater than the second distal end diameter.

15. The biological sample collection system of claim 13, wherein the third proximal end diameter is greater than the fourth distal end diameter.

16. The biological sample collection system of claim 13, wherein the third proximal end diameter is greater than the second distal end diameter.

17. The biological sample collection system of claim 13, wherein the third proximal end diameter is greater than the first proximal end diameter.

18. The biological sample collection system of claim 13, wherein the second distal end diameter is substantially equal to the fourth distal end diameter.

19. The biological sample collection system of claim 12, wherein a frictional force between the outer sleeve and the inner vessel is less than a mechanical force required to secure the sealing cap to the sample collection vessel.

20. A kit for collecting and preserving a biological sample, the kit comprising:
  a sample collection vessel, the sample collection vessel comprising:
    a sample collection chamber having an opening configured to receive the biological sample from a user into the sample collection chamber, the opening being defined by a rim of the sample collection vessel and the rim having an inner diameter;
    a connection member disposed on an exterior portion the sample collection vessel and adjacent to the opening; and
    an interior sidewall;
  a sealing cap, the sealing cap comprising:
    a reagent chamber configured to store a reagent; and
    a complementary connection member configured to engage the connection member of the sample collection vessel; and
  wherein the sealing cap is securable to the sample collection vessel and is carrying a sleeve valve having a closed configuration and an open configuration, the sleeve valve comprising:
    an inner vessel comprising a fluid vent, the inner vessel in fluid communication with the reagent chamber of the sealing cap, and
    an outer sleeve surrounding the inner vessel and forming a fluid-tight fit with the inner vessel, the outer sleeve comprising a first section and a second section, the first section having a first diameter larger than the inner diameter and the second section having a second diameter equal to or smaller than the inner diameter;
  wherein, in the closed configuration of the sleeve valve, the outer sleeve is positioned to obstruct the fluid vent,
  wherein the sleeve valve is configured to be movable to the open configuration in response to the sealing cap being secured to the sample collection vessel, and
  wherein, in the open configuration, the second section is in contact with the interior sidewall of the sample collection vessel and the first section of the outer sleeve is pushed by the rim of the sample collection vessel, thereby moving the outer sleeve relative to the inner vessel to reveal the fluid vent to allow the reagent to flow from the reagent chamber into the sample collection chamber, thereby dispensing the reagent into the sample collection chamber.

21. The kit of claim 20, further comprising a funnel configured to associate with the sample collection vessel and to guide receipt of a biological sample from a user into the sample collection chamber of the sample collection vessel.

22. A biological sample collection system, the system comprising:
- a sample collection vessel, the sample collection vessel comprising a sample collection chamber having an opening configured to receive a biological sample into the sample collection chamber and a ring structure formed on an interior sidewall of the sample collection vessel; and
- a sealing cap, the sealing cap comprising a reagent chamber and carrying a sleeve valve, the reagent chamber configured to store a reagent therein, the sleeve valve having a closed configuration and an open configuration, the sleeve valve comprising:
  - an inner vessel comprising a fluid vent, the inner vessel in fluid-tight communication with the reagent chamber of the sealing cap, and
  - an outer sleeve surrounding and in fluid-tight communication with the inner vessel, the outer sleeve comprising a first section and a second section, the first section having a first diameter larger than the inner diameter and the second section having a second diameter equal to or smaller than the inner diameter, and having a guide member associated with a guide channel of the sealing cap and a detent formed on the second section of the outer sleeve,
  - wherein, in the closed configuration of the sleeve valve, the outer sleeve is positioned to obstruct the fluid vent,
  - wherein the sleeve valve is configured to be movable to the open configuration in response to the sealing cap being secured to the sample collection vessel, and
  - wherein, in the open configuration, the second section is in contact with the interior sidewall of the sample collection vessel and the first section of the outer sleeve is pushed by the sample collection vessel, thereby moving the outer sleeve relative to the inner vessel to reveal the fluid vent to allow the reagent to flow from the reagent chamber to the sample collection chamber, thereby dispensing the reagent into the sample collection chamber,
  - wherein the ring structure is configured to temporarily retain the outer sleeve in a fixed position relative to the sample collection vessel, and
  - wherein the inner vessel is configured to move relative to the outer sleeve to unseal and reseal with the outer sleeve.

23. The biological sample collection system of claim 1, wherein the first section corresponds to a body of the outer sleeve and the second section corresponds to a lower collar of the outer sleeve.

24. The biological sample collection system of claim 1, wherein the fluid-tight fit is an interference fit.

25. The kit of claim 20, wherein the first section corresponds to a body of the outer sleeve and the second section corresponds to a lower collar of the outer sleeve.

26. The kit of claim 20, wherein the fluid-tight fit is an interference fit.

27. The biological sample collection system of claim 22, wherein the first section corresponds to a body of the outer sleeve and the second section corresponds to a lower collar of the outer sleeve.

* * * * *